(12) United States Patent
Lundgren et al.

(10) Patent No.: US 7,172,574 B2
(45) Date of Patent: Feb. 6, 2007

(54) TRANSCUTANEOUS PORTAL DEVICE

(75) Inventors: Dan Lundgren, Hovås (SE); Rickard Nyman, Uppsala (SE)

(73) Assignee: Transcutan AB, Vallingby (SE)

( * ) Notice: Subject to any disclaimer, the term of this patent is extended or adjusted under 35 U.S.C. 154(b) by 71 days.

(21) Appl. No.: 10/506,673

(22) PCT Filed: Apr. 2, 2003

(86) PCT No.: PCT/SE03/00527

§ 371 (c)(1),
(2), (4) Date: Sep. 17, 2004

(87) PCT Pub. No.: WO03/086527
PCT Pub. Date: Oct. 23, 2003

(65) Prior Publication Data

US 2005/0119637 A1    Jun. 2, 2005

(30) Foreign Application Priority Data

Apr. 8, 2002   (SE)   .................................. 0201054

(51) Int. Cl.
*A61M 31/00* (2006.01)
(52) U.S. Cl. .................................. 604/93.01; 604/175
(58) Field of Classification Search ............ 604/93.01, 604/164.01, 167.01, 167.02, 167.06, 175, 604/256, 905, 910; 606/108, 191
See application file for complete search history.

(56) References Cited

U.S. PATENT DOCUMENTS

| | | | |
|---|---|---|---|
| 4,781,693 A | | 11/1988 | Martinez et al. |
| 5,338,314 A | * | 8/1994 | Ryan ........................... 604/284 |
| 5,350,364 A | * | 9/1994 | Stephens et al. ........ 604/167.06 |
| 5,484,425 A | * | 1/1996 | Fischell et al. ............. 604/528 |
| 5,591,137 A | * | 1/1997 | Stevens ....................... 604/296 |
| 5,743,883 A | * | 4/1998 | Visconti ................. 604/167.02 |
| 5,944,697 A | | 8/1999 | Biche |
| 6,036,672 A | * | 3/2000 | Allen et al. ............ 604/167.02 |

FOREIGN PATENT DOCUMENTS

| | | |
|---|---|---|
| WO | 87/06122 | 10/1987 |
| WO | 89/06987 | 8/1989 |
| WO | 97/15338 | 5/1997 |

* cited by examiner

*Primary Examiner*—LoAn H. Thanh
(74) *Attorney, Agent, or Firm*—Jacobson Holman PLLC

(57) ABSTRACT

A transcutaneous portal arrangement including a portal body having a bottom wall with a through-passing opening or transit for accommodating a catheter. A tubular element that fits in the portal body includes an end-portion which is inserted into the end-portion of the catheter. A clamping structure clamps the end-portion of the tubular element against the bottom wall around the through-passing opening so as to sealingly clamp the outer wall and the inner wall of the catheter around the edge of the opening and around the periphery of the tubular element, respectively.

19 Claims, 1 Drawing Sheet

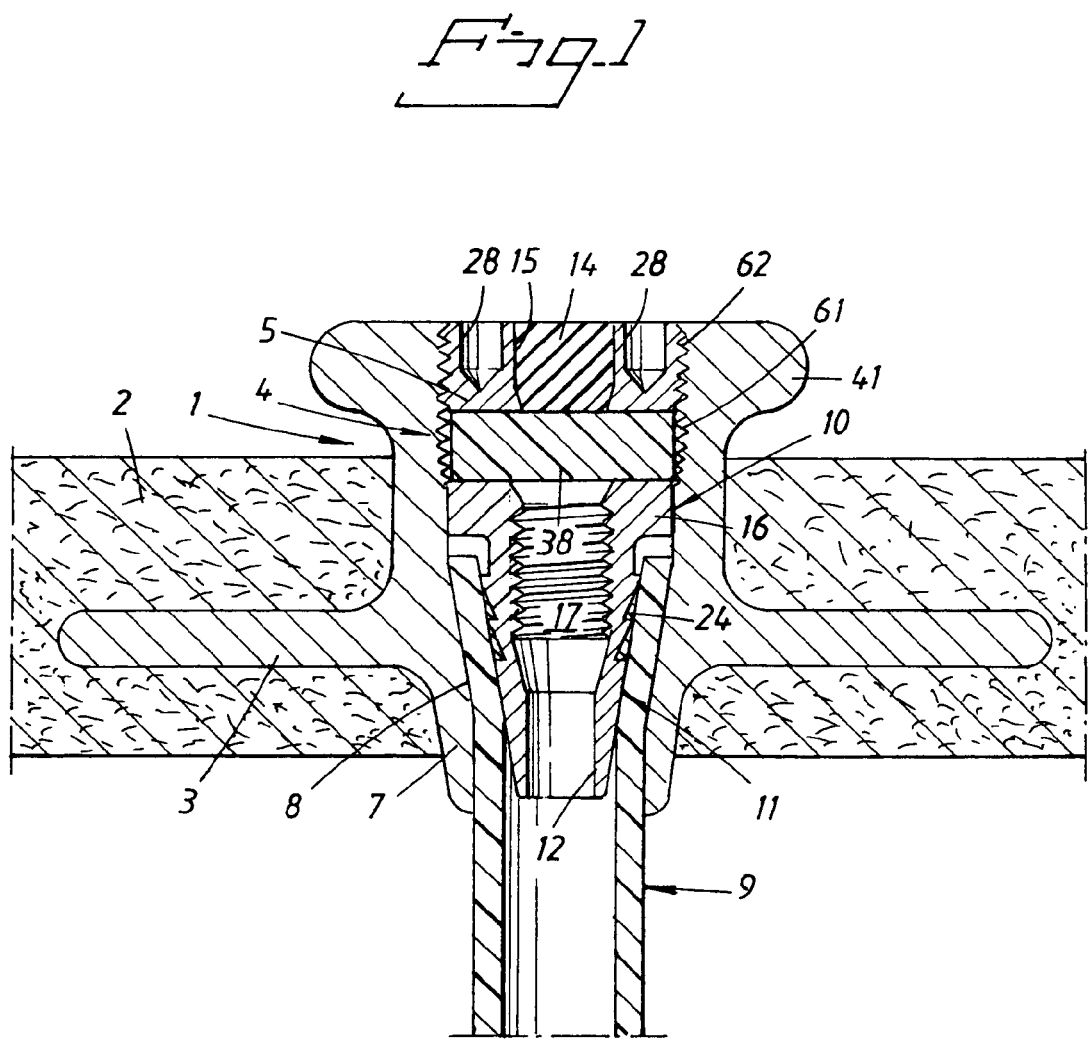

TRANSCUTANEOUS PORTAL DEVICE

This is a nationalization of PCT/SE03/00527 filed Apr. 2, 2003 and published in English.

BACKGROUND OF THE INVENTION

1. Field of the Invention

The present invention relates to a transcutaneous portal device including a portal body that includes a recess delimited by a peripheral wall and a bottom wall that includes a through-passing opening which receives a catheter. A tubular element has an end-portion which is inserted into the end-portion of the catheter. The portal arrangement includes clamping means for clamping the end-portion of the tubular element against the bottom wall around the through-passing opening so as to tightly clamp the outer and the inner wall of the catheter around the edge of the opening and around the periphery of the end-portion of the tubular element respectively.

2. Description of the Related Art

WO-89/06897 teaches a transcutaneous portal device that includes a sealing coupling or union for releasably connecting in the portal one end part of an outer conduit and one end part of a catheter. The catheter extends into the body interior.

The portal itself, which is also described in PCT SE-87/00201 for instance, is suitably comprised of titanium and has generally the form of a cup whose wall carries on its outside a ring flange that preferably includes slots and openings that facilitate stable tissue ingrowth. The upper edge portion of the cup carries a thread, which co-acts with a corresponding thread on a cap or lid. An elastic sealing plug can be inserted into the cup so as to essentially fill-out the same. The body can be compressed axially with the aid of the cap thread joint, wherewith the body swells radially and seals against and around the inner wall of the cup, therewith effectively closing the central channel in the plug. An outer conduit can be forced through the plug channel and therewith placed in communication with the bottom space of the cup beneath the plug.

A catheter extends through an opening in the bottom wall of the cup/portal. Resting on the inner side of the bottom wall is a plate that includes an opening for the end portion of the catheter. This catheter end portion includes a head, which prevents the catheter from being drawn out through the plate opening.

When the cap or lid has been opened and the plug removed, the plate can be gripped and lifted up and the catheter therewith drawn out through the portal via the bottom opening.

The bottom wall includes on the outside around the transit opening a nipple to which a hose is fitted. The inner diameter of the hose is slightly larger than the outer diameter of the catheter, so as to form a gap seal therebetween. The gap seal between portal and the patient's body must be sufficiently large to enable the catheter to be readily drawn through the hose both with regard to insertion and withdrawal.

SUMMARY OF THE INVENTION

One object of the present invention is to provide a portal arrangement which provides a simple and safe construction for sealing of the outer periphery of the catheter against the bottom wall of the portal.

Another object is to design said construction so that it can include a membrane that sealingly screens a sleeve which is connected sealingly to the catheter and which can be pierced by an injection needle for injection of a chosen substance into and through the catheter.

A further object is to provide a construction with which the catheter can be removed comfortably and replaced after having been cleaned, or replaced with a fresh catheter.

These objects are achieved either fully or partially by the invention.

The present invention achieves these objects by providing a transcutaneous portal arrangement having a portal body that includes a recess delimited by a peripheral wall and a bottom wall that includes a through-passing opening which receives a catheter. A tubular element has an end-portion which is inserted into the end-portion of the catheter, and the portal arrangement includes a clamping structure for clamping the end-portion of the tubular element against the bottom wall around the through-passing opening so as to tightly clamp the outer and the inner wall of the catheter around the edge of the opening and around the periphery of the end-portion of the tubular element, respectively. The clamping structure includes a screw which is rotatable relative to the tubular element. The screw has an external screw thread which co-acts with an internal screw thread on the peripheral wall of the recess. The tubular element, which has a coupling part that can be coupled to a tool for withdrawal of the tubular element from the portal body, is connected to the catheter for entraining the catheter as the tubular element is withdrawn from the portal body.

An important feature of the present invention resides in the catheter end portion, which consists of a springy elastic material, such as a plastic material, being pressed sealingly against the bottom wall around its transit opening, while, at the same time, sealing the connecting inner periphery of the catheter around a tubular element inserted into the catheter end portion. This tubular element can be tightened down against the bottom wall of the portal, for instance with the aid of a thread joint, so as to clamp the catheter hose sealingly around its periphery between the tubular element and the edge of the opening through the bottom wall.

In one preferred embodiment of the invention, the tubular element has a conical end which is inserted into the catheter hose and which tapers in a direction towards the bottom wall. Moreover, the transit opening in the bottom wall has a conical shape so that the clamping forces will propagate along a longitudinal section of the catheter hose when the conical parts of the sleeve and the transit opening mutually co-act axially.

In one preferred embodiment of the invention, the through-passage channel of the tubular element is screened by a sealing element. This sealing element may have the form of a piercable self-sealing membrane. The membrane can thus be penetrated with a canula of an injection syringe to allow a pharmaceutical preparation to be injected into a patient through the catheter.

The end portion of the tubular element inserted into the end of the catheter may be joined to the catheter by means of a glue joint or some other appropriate joint which will permit the catheter to accompany the tubular element as it is withdrawn from the portal. The catheter and the tubular element will conveniently be fixed to one another upon delivery. As a result of the inventive construction, the transit opening in the bottom wall of the portal will be sealingly screened.

The invention will now be described by way of example and with reference to the accompanying drawing.

BRIEF DESCRIPTION OF THE DRAWING

FIG. 1 is a schematic axial section view of a portal arrangement according to the invention.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

FIG. 1 shows a portal whose body 1 is anchored to a layer of tissue 2 (for instance the abdominal wall) in a known manner. The portal body 1 has a generally cupped shape that faces outwards. The portal body also includes a peripherally extending outer anchoring flange 3 that includes openings (not shown) which ensure that the body 1 will be anchored in the tissue 2 particularly securely. Provided in the bottom wall 7 of the portal body 1 is a transit opening 8 for accommodating a catheter hose 9. The opening 8 is shown to narrow conically in an inward direction. The free diameter of the opening 8 is slightly larger than the outer diameter of the catheter 9 so as to allow the catheter to be inserted comfortably through the opening 8. A tubular element 10, i.e. a sleeve, has an external conical end-portion 11 which is received in the end-portion of the catheter 9. The sleeve 10 and the catheter 9 are preferably joined together. The join is conveniently sealingly arranged around the periphery of said end-portion 11 and may have the form of a glue joint, a weld joint, or a joint connection of the kind shown in FIG. 1, where the accommodated end of the catheter clamps elastically against the periphery of the end 11 of the sleeve and one or more sleeve-carried beads 24, preferably disposed around the periphery of the end of said sleeve. The beads 24 may have the form of barbs or flukes that are orientated to make withdrawal of the catheter from the sleeve 10 difficult to achieve. The conicity of the end of the tubular sleeve 10 corresponds to the conicity of the transit opening 8. The conicity may be in the order of 10°.

The illustrated sleeve 10 includes at its outer end a ring flange 16 whose edge lies in close proximity to the inner barrel wall surface of the body 1 so as to centralise the outer end-portion of the sleeve in the body 1. The end-portion 11 of the sleeve 10 is centred in the bottom opening 8 via the catheter hose 9. The inner wall of the body includes at its outer end an internal thread 61. Received in the body 1 is a screw 5 that has an outer thread 62 which co-acts with the inner thread 61. The screw 5 includes on its outer part a driver 28, which has the form of a recess in the illustrated case. The screw 5 can be rotated relative to the body 1 with the aid of a tool that has corresponding formations (pins). A washer or plate 38 whose outer diameter corresponds to the inner diameter of the body 1 is placed between the sleeve 10 and the screw. The cylindrical washer is conveniently comprised of an elastomeric material, or at least in its central region.

The screw 5 has a central through-passing opening 15 which tapers conically in a direction towards the sleeve 10 and which is preferably filled with and sealingly screened by an elastic body 14.

As illustrated, the through-passing channel 12 of the sleeve 10 includes coupling means 17 in the form of an inner thread at its outer part.

Rotation of the screw 5 with the aid of an appropriate tool results in an axial pressure against the sleeve 10, causing the end-portion of the catheter hose 9 to be wedged firmly between the conical end-portion 11 of the sleeve 10 and the corresponding conical wall of the bottom opening 8, so that the inner periphery of the hose 9 will seal against the end-portion 11 of the sleeve and the outer periphery of the hose will seal against the wall of the opening 8. An injection cannula can be inserted through the body 14 and the washer 38 for insertion of a fluid into the catheter hose 9 via the through-passing channel 12 of the sleeve 10. The bodies 14, 38 will preferably be self-sealing in a known manner, when withdrawing the cannula.

The catheter hose 9 can be withdrawn for replacement or for cleaning purposes, by dismantling the screw 5 and the washer 38 and then connecting a tool that has an externally threaded end-portion to the internal thread 17 of the sleeve, whereafter the sleeve 10 can be withdrawn from the body 1 together with the catheter hose 9.

The catheter hose 9 may be replaced over a line guide in a known manner, wherein the tool is conveniently designed to provide free passage to the line guide. The person skilled in this art will be aware that the sleeve 10 can be clamped adjustably against the end-portion of the hose 9 with the aid of clamping means other than the screw 5 and the internal thread 61 of the body.

The opening 15 of the screw 5 is shown to have a conical shape that narrows in a direction towards the sleeve 10 so as to function as a guide for a cannula as it is inserted through the opening 15 and the washer 38 into the through-passing channel 12. The conicity of the opening 15 may be roughly the same as that shown in the drawing, and has a smallest diameter that corresponds to the free diameter of the through-passing channel 12. The washer 38 may, of course, be joined to the screw 5 and the elastomeric material of said washer may be integral with the elastic body 14 in the through-passing channel 15 of the screw 5.

The illustrated body 1 has an outer edge bead 41 of enlarged diameter, and a lid or cover (not shown) may be provided for releasably screening the outer end-portion of the body 1.

The membrane 14 may be associated or affiliated with the flange 16, and a possible join between sleeve 10 and flange 16 will preferably be made tight by pressing the flange and the sleeve against each other. For example the flange 16 and the lower part of the sleeve may be separate elements that together establish a tight join that enables the flange 16 and the lower part of the sleeve to be rotated relative to one another. The join may conveniently be rotation-symmetrical relative to the centre axis of the sleeve 10 around which the sleeve rotates generally symmetrically. The join is conveniently formed to hold the upper end of the lower part of the sleeve centred in the portal arrangement.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A transcutaneous portal arrangement comprising:
   a portal body that includes a recess defined by a peripheral wall and a bottom wall that includes a conically tapered through-passing opening which receives a catheter having an outer wall and an inner wall;

a tubular element within said recess having a conically-tapered end-portion which is inserted into an end-portion of the catheter and connected thereto for entraining said catheter as the tubular element is withdrawn from the portal body, the conical taper of said end-portion generally corresponding with the conical taper of said opening; and a clamping structure configured to clamp the conically-tapered end-portion of the tubular element with said catheter end-portion connected thereto against the bottom wall around the conically tapered through-passing opening so as to clamp said catheter outer wall around an edge of the opening and said catheter inner wall around a periphery of the end-portion of the tubular element.

2. The portal arrangement according to claim 1, wherein said tubular element includes a coupling part that can be coupled to a tool for withdrawal of the tubular element from the portal body along with the catheter connected thereto.

3. The portal arrangement according to claim 2, wherein said coupling part includes an internal thread on the inside of the tubular element, and said tool includes an external thread that co-acts with said internal thread.

4. The portal arrangement according to claim 1, wherein said clamping structure includes a screw which is rotatable relative to the tubular element, said screw having an external screw thread which co-acts with an internal screw thread on the peripheral wall of the recess.

5. The portal arrangement according to claim 1, wherein said tubular element includes a through-passing channel which is screened by a sealing element that can be pierced by the cannula of an injection syringe and that is self-sealing subsequent to withdrawal of the cannula.

6. The portal arrangement according to claim 5, wherein said sealing element includes an elastomeric insert located between the screw and the tubular element so that in response to compression between said screw and said tubular element, the insert seals against the screw and the tubular element and also against an inner wall of the portal body.

7. The portal arrangement according to claim 4, wherein the screw includes a through-passing opening that tapers conically in a direction towards the tubular element.

8. The portal arrangement according to claim 7, wherein the through-passing opening of said screw is screened by a body of a piercable self-sealing material.

9. The portal arrangement according to claim 1, wherein the end-portion of the catheter is affixed to the tubular element by a joint so that the catheter hose will be entrained axially by the tubular element upon the withdrawal of said element from said body.

10. The portal arrangement according to claim 1, wherein the screw is separate from the tubular element.

11. The portal arrangement according to claim 1, wherein at least the catheter end-portion joined to the tubular element is made of an elastomeric material.

12. The portal arrangement according to claim 1, wherein said portal body is adapted for implantation in a body of a user.

13. The portal arrangement according to claim 12, wherein said tapered portions narrow toward an interior of said body.

14. A transcutaneous portal arrangement comprising:

a portal body that includes a recess defined by a peripheral wall and a bottom wall that includes a through-passing opening which receives a catheter having an outer wall and an inner wall;

a tubular element within said recess and adjacent said bottom wall, said tubular element having a through-passing channel and an end-portion which is inserted into an end-portion of the catheter and connected thereto;

an elastomeric sealing element on top of said tubular element and covering said through-passing channel; and a clamping structure configured to press said sealing element against said tubular element and clamp the end-portion of the tubular element with said catheter end-portion connected thereto against the bottom wall around the through-passing opening so that said catheter outer wall is clamped around an edge of the opening and said catheter inner wall is clamped around a periphery of the end-portion of the tubular element.

15. The portal arrangement according to claim 14, wherein said clamping structure includes a screw which is rotatable relative to the tubular element, said screw having an external screw thread which co-acts with an internal screw thread on the peripheral wall of the recess.

16. The portal arrangement according to claim 14, wherein said tubular element tapers conically toward said opening and said bottom wall has a corresponding taper.

17. The portal arrangement according to claim 14, wherein said sealing element has a pierceable central portion and an exterior thread which engages an inner thread of said peripheral wall.

18. The portal arrangement according to claim 14, wherein said clamping structure includes a screw having a through-passing opening screened by a second sealing element, both of said sealing elements being pierceable by a needle to provide access to an interior of said catheter.

19. The portal arrangement according to claim 14, wherein said portal body is adapted for implantation in a body of a user.

* * * * *